United States Patent [19]  [11] 4,201,706
Trager et al.  [45] May 6, 1980

[54] TREATMENT OF CORNEAL EDEMA

[75] Inventors: Seymour F. Trager, Plainview, N.Y.; Keith Green, Augusta, Ga.

[73] Assignee: Burton, Parsons & Company, Inc., Washington, D.C.

[21] Appl. No.: 944,735

[22] Filed: Sep. 22, 1978

[51] Int. Cl.² .................. A61K 31/74; A61K 31/79; A61K 31/045

[52] U.S. Cl. .................................. 424/78; 424/80; 424/343

[58] Field of Search .................. 424/78, 343, 80

[56] References Cited

U.S. PATENT DOCUMENTS

| 2,703,777 | 3/1955 | Feinstein et al. | 424/153 |
| 2,992,970 | 7/1961 | Baptist et al. | 424/343 |
| 3,200,039 | 8/1965 | Thompson | 424/14 |
| 3,767,788 | 10/1973 | Rankin | 424/78 |

OTHER PUBLICATIONS

Chem. Abst. 80, 158(j) (1974)–Bartkowska et al.
Chem. Abst. 80, 144050(r) (1974)–Obazawa et al.

Primary Examiner—Douglas W. Robinson
Attorney, Agent, or Firm—Fidelman, Wolffe & Waldron

[57] ABSTRACT

An ophthalmic solution useful for the reduction of corneal edema is provided. The preparation comprises an aqueous solution of pentahydric or hexahydric alcohols in optional combination with other eye-treating ingredients. Examples of appropriate alcohols include sorbitol, inositol, and xylitol with sorbitol being especially preferred.

9 Claims, No Drawings

TREATMENT OF CORNEAL EDEMA

BACKGROUND OF THE INVENTION

1. Field of the Invention

This invention relates generally to ophthalmic solutions and methods for their use. More specifically, this invention relates to the reduction of corneal edema by the topical treatment thereof using ophthalmic solutions of specific composition.

2. Description of the Prior Art

Corneal edema often results from physical trauma or irritation and is also observed in association with diseases such as glaucoma. This condition results in blurred vision and can even lead to the essential loss of vision.

One common therapy approach to the management of corneal edema involves the use of topically applied hypertonic solutions. Many of the most effective prior art compositions utilize sodium chloride as the active ingredient. In order to be effective however, the sodium chloride concentration must be relatively high, on the order of 5%, a level which is about the maximum which can be tolerated by the normal human eye.

Experimental results obtained by treatment of human subjects with a variety of hypertonic agents are reported in an article by Luxenberg and Green, entitled "Reduction of Corneal Edema with Topical Hypertonic Agents", published in the *American Journal of Ophthalmology*, Vol. 71, No. 4, pp. 847-853 (1971). Those researchers investigated seven different hypertonic agents which listed in decreasing order of effectiveness are: 1. 5% sodium chloride ointment containing petrolatum and lanolin; 2. A buffered aqueous emulsion containing 5% sodium chloride and 5% glycerine; 3. a solution containing 5% sodium chloride with 5% gum cellulose and 2% glycerine; 4. a 30% sodium sulfacetamide solution in polyvinyl alcohol; 5. a 5% gum cellulose solution; 6. corn syrup containing sucrose, dextrose, and salt; and 7. a solution containing 0.9% methyl cellulose with 5% sodium chloride. As much as a 20% reduction in corneal thickness was observed with use of the 5% sodium chloride ointment. It was postulated that the ointment caused an osmotic withdrawal of fluid from the cornea thereby reducing its thickness and increasing its transparency.

Another article by Green and Downs entitled "Reduction of Corneal Thickness with Hypertonic Solutions" published in the *American Journal of Ophthalmology*, Vol. 75, No. 3, pp. 507-510, (1973), presented results obtained in experiments carried out with adult albino rabbits whose eyes had not previously been used experimentally. That work established the appropriateness of rabbits as experimental animals for this purpose and a comparison of the data presented in the two publications established that the effect of a hypertonic agent when applied to a human eye is approximately double that of the same agent when applied to a rabbit eye.

Ophthalmic solutions in general are well known and commonly used, particularly as contact lens wetting solutions. The solutions commonly comprise a mixture of one or more alkali metal salts, viscosity building agents, wetting agents and humectants, and medicaments of various kinds. Glycerine is a commonly used humectant but sorbitol and propylene glycol have also been suggested as humectants in ophthalmic solutions as is shown in U.S. Pat. No. 2,703,777. However, there is no recognition in the art that pentahydric and hexahydric alcohols such as sorbitol function to reduce corneal edema.

SUMMARY OF THE INVENTION

An ophthalmic solution containing therapeutically effective amounts of pentahydric or hexahydric alcohols and adapted for topical application reduce corneal edema without ocular distress or irritation. Alcohols appropriate for use as a therapeutically active ingredient include sorbitol, inositol, and xylitol. Of these alcohols, sorbitol is preferred as it is the most effective in reducing corneal edema. Simple solutions of the alcohols in distilled water may be used in the practice of this invention, but it is preferred to dissolve the alcohols in a base solution of another ophthalmic solution. Treatment is accomplished by the periodic application of the composition to the external ocular surface.

Hence, it is an object of this invention to provide an ophthalmic solution effective to reduce corneal swelling.

It is another object of this invention to provide a method for the reduction of corneal edema.

Yet another objective of this invention is to relieve corneal edema without concomitant eye irritation caused by hypertonic solutions containing high concentrations of sodium chloride.

DETAILED DESCRIPTION OF THE INVENTION

It has been found that pentahydric and hexahydric alcohols exemplified by sorbitol, inositol and xylitol are therapeutically effective to reduce corneal edema. Solutions of the alcohols are topically applied to the cornea surface and are believed to act by an osmotic withdrawl of fluid from the cornea thus reducing swelling. The alcohols may be administered as a simple solution in distilled water but it is preferred that the alcohols be dissolved in base solutions such as those which provide lubricating and cushioning effects for contact lenses.

Particularly preferred base solutions are the ophthalmic solutions described in U.S. Pat. No. 3,767,788 to Rankin which is hereby incorporated by reference. This patent describes aqueous ophthalmic solution containing about 0.05-2% by weight of polyethylene oxides having molecular weights of at least 100,000 to provide a viscosity of 0-3,000 cps at 20° C., plus polyalkylene glycols, preferably polyethylene glycol, in amounts ranging from 500-5,000 weight percent based on the weight of the polyethylene oxide, together with other optional components. As recited in the patent, there may be included: pH buffers such as sodium borate or mono- and di-sodium phosphates, or salts such as other alkali-metal phosphates, carbonates and acetates; mechanical buffers or viscosity controlling agents such as water soluble eye compatible cellulose derivatives; eye compatible non-ionic surfactants; polyvinylpyrrolidone; and eye compatible biocides.

The alcohols useful in this invention are all crystalline solids with a sweet taste and are freely soluble in water. Sorbitol is a six-carbon alcohol with one hydroxyl group attached to each carbon atom while xylitol is a five-carbon alcohol of similar structure. Inositol is a hexahydric alcohol derived from cyclohexane in which one hydroxyl group is attached to each carbon atom. As used in this specification, all geometrical and stereo isomers of these alcohols are included within the scope of the invention.

Concentration of the alcohol may be varied over a fairly broad range depending upon the activity desired. Concentrations ranging from about 300 mM to about 1 M are appropriate for most routine uses of the composition. When using sorbitol for example, a concentration of about 600 mM produces therapeutic effects generally equivalent to that obtained by use of a 5% sodium chloride ointment. Inositol and xylitol display somewhat less activity than does sorbitol and their effect tends to be shorter in duration. Thus, sorbitol is generally preferred.

A series of tests were performed using rabbits as subjects to show the effect of the disclosed alcohol solutions in reducing corneal swelling. A description of these tests and the results obtained are set out in the following example:

EXAMPLE

Solutions of various pentahydric and hexahydric alcohols having a concentration of 600 mM in Adsorbobase were prepared. Adsorbobase is an ophthalmic solution prepared according to the teachings of U.S. Pat. No. 3,767,788 and is available from Burton Parsons Chemicals, Inc., Washington, D.C.

Each solution was tested on the eyes of six normal rabbits. The rabbits receive a 50 μl drop of the active solution applied to the external ocular surface at the 12 o'clock position and allowed to run over the cornea. Corneal thickness was measured at 60 minute intervals following the measurement of an initial stable thickness and the subsequent instillation of the solution. The data obtained, expressed in terms of average percentage reduction in corneal thickness are shown in the following table:

TABLE 1

| Time (minutes) | 0 | 60 | 120 | 180 | 240 | 300 | 360 |
|---|---|---|---|---|---|---|---|
| | | Percent Reduction in Thickness | | | | | |
| Sorbitol | 0 | 7.4 | 8.5 | 9.7 | 7.4 | 4.8 | 4.6 |
| Inositol | 0 | 3.9 | 5.5 | 5.5 | 3.2 | 0.5 | 0.1 |
| Xylitol | 0 | 1.1 | 5.7 | 4.1 | 4.1 | 2.5 | — |

A comparison of these data to the efficacy of sodium chloride-based hypertonic compositions using rabbits as experimental subjects is as follows:

TABLE 2*

| Time (minutes) Composition | 0 | 60 | 120 | 180 | 240 | 300 | 360 |
|---|---|---|---|---|---|---|---|
| | | Percent Reduction in Thickness | | | | | |
| B & K Solution[1] BP-E | 0 | 4.0 | 2.29 | 2.29 | 1.14 | 1.71 | +0.57 |
| Ocular[2] | 0 | 4.57 | 2.86 | 2.86 | 3.43 | 2.86 | 1.14 |

*Data taken from Green and Downs, American Journal of Ophthalmology, Vol. 75, No. 3, p. 508 (1973)
[1]Burris and Kemp solution which is a solution of 5% NaCl with 5% gum cellulose and 2% glycerin.
[2]An experimental agent consisting of 5% NaCl and 5% glycerin in a buffered aqueous emulsive vehicle.

A further comparison of these data to the efficacy of sodium chloride-based hypertonic compositions using human subjects is as follows:

TABLE 3*

| Time (minutes) Composition | 0 | 60 | 120 | 180 | 240 | 300 | 360 |
|---|---|---|---|---|---|---|---|
| | | Percent Reduction in Thickness | | | | | |
| B & K Solution BP-E | 0 | 8.9 | 3.9 | 1.7 | — | — | — |
| Ocular NaCl | 0 | 8.4 | 7.7 | 7.7 | 4.2 | 1.1 | — |
| Ointment[3] | 0 | 15 | 16.8 | 20.5 | 21.2 | 15.7 | 14.2 |

*Data taken from Luxenberg and Green, American Journal of Ophthalmology, Vol. 71, No. 4, pp. 850-851 (1971).
[3]A 5% NaCl ointment containing petrolatum and lanolin.

As may be seen from a comparison of the data presented in Tables 2 and 3, the effect of hypertonic agents on human eyes is about twice that observed on rabbit eyes in terms of reduction in corneal thickness. Thus, the results obtained by use of the preparations of this invention, expecially those compositions containing sorbitol, are equally efficacious as any conventional agents and superior to most.

During all of the experimental studies the rabbits were carefully monitored for any signs of ocular distress including conjunctival and palpebral hyperemia, iris hyperemia and pupil reflex, epithelial and palpebral lesions and edema, stromal edema and cells and flare in aqueous. Eyes receiving the solutions were entirely free of any signs of irritation.

On two occasions, drops of sorbitol (600 mM) in Adsorbobase were topically applied to human eyes with no feeling of pain or inducement of ocular irritation. These observations are consistant with previous findings (U.S. Pat. No. 2,992,970) that aqueous solutions of sorbitol having a concentration of 25% or more do not cause irritation or burning of fissures in rectal mucosa.

We claim:

1. A method for reducing corneal edema comprising topically applying to the cornea an aqueous ophthalmic solution comprising a therapeutically effective amount of a compound selected from the group consisting of sorbitol, inositol, xylitol, and mixtures thereof.

2. The method of claim 1 wherein the concentration of said compound is in the range of 300 mM to 1 M.

3. The method of claim 2 wherein said solution also contains from about 0.05 to about 2.0% by weight of an ethylene oxide polymer having a molecular weight of at least 100,000 and sufficient to provide a viscosity of less than about 30,000 cps, and from about 100 to about 5,000 weight percent based on the ethylene oxide polymer of polyalkylene glycol, said solution may contain, in addition, one or more of the members selected from the group consisting of an eye compatible pH buffer, from 0 to about 0.5% of an eye compatible non-ionic surfactant, from 0 to 5% by weight of polyvinylpyrrolidone and an eye compatible biocide.

4. The method of claim 3 wherein said compound is sorbitol.

5. The method of claim 4 wherein the sorbitol concentration is approximately 600 mM.

6. The method of claim 3 wherein said compound is inositol.

7. The method of claim 6 wherein the inositol concentration is approximately 600 mM.

8. The method of claim 3 wherein said compound is xylitol.

9. The method of claim 8 wherein the xylitol concentration is approximately 600 mM.

* * * * *